(12) United States Patent
Cornelius et al.

(10) Patent No.: US 7,266,414 B2
(45) Date of Patent: Sep. 4, 2007

(54) METHODS AND DEVICES FOR CREATING ELECTRICAL BLOCK AT SPECIFIC SITES IN CARDIAC TISSUE WITH TARGETED TISSUE ABLATION

(75) Inventors: Richard Cornelius, Wayzata, MN (US); William Swanson, St. Paul, MN (US)

(73) Assignee: Syntach, AG, Schaffhausen (CH)

( * ) Notice: Subject to any disclaimer, the term of this patent is extended or adjusted under 35 U.S.C. 154(b) by 0 days.

(21) Appl. No.: 10/971,452

(22) Filed: Oct. 22, 2004

(65) Prior Publication Data

US 2005/0090820 A1    Apr. 28, 2005

Related U.S. Application Data

(60) Provisional application No. 60/514,428, filed on Oct. 24, 2003.

(51) Int. Cl.
    *A61B 18/18*    (2006.01)
    *A61N 1/00*    (2006.01)
(52) U.S. Cl. .................................. 607/122; 606/41
(58) Field of Classification Search .............. 606/41, 606/47–50; 607/101, 102, 122
    See application file for complete search history.

(56) References Cited

U.S. PATENT DOCUMENTS

| | | | |
|---|---|---|---|
| 4,016,886 A | 4/1977 | Doss et al. | |
| 4,580,568 A | 4/1986 | Gianturco | |
| 5,176,135 A | 1/1993 | Fain et al. | |
| 5,234,448 A | 8/1993 | Wholey et al. | |
| 5,254,127 A | 10/1993 | Wholey et al. | |
| 5,281,218 A | 1/1994 | Imran | |
| 5,312,456 A | 5/1994 | Reed et al. | |
| 5,360,440 A | 11/1994 | Andersen | |
| 5,370,675 A * | 12/1994 | Edwards et al. ............ 607/101 |
| 5,403,311 A | 4/1995 | Abele et al. | |
| 5,423,851 A | 6/1995 | Samuels | |
| 5,507,779 A | 4/1996 | Altman | |
| 5,509,924 A | 4/1996 | Paspa et al. | |

(Continued)

FOREIGN PATENT DOCUMENTS

EP    0 497 620 A2    8/1992

(Continued)

OTHER PUBLICATIONS

*The Thoracic And Cardiovascular Surgeon*, III Supplement, vol. 47, Aug. 1999, pp. 347-351 "An Anatomic Approach To Prevention Of Atrial Fibrillation: Pulmonary Vein Isolation With Through-The-Balloon Ultrasound Ablation (TTB-USA)".

(Continued)

*Primary Examiner*—Michael Peffley
(74) *Attorney, Agent, or Firm*—Inskeep IP Group, Inc.

(57) ABSTRACT

In one embodiment, the present invention provides a bipolar ablation device with multiple needle electrodes that penetrate a desired target tissue. These electrodes may be arranged in a variety of therapeutically effective arrangements, such as a comb-like shape, a multi-needle wheel, or an expanding bow design. By contacting and preferably penetrating the cardiac tissue with bipolar electrodes, a user can more precisely create ablation-induced scarring and thus electrical block at desired target locations without causing unwanted damage and related complications.

6 Claims, 7 Drawing Sheets

U.S. PATENT DOCUMENTS

| | | |
|---|---|---|
| 5,531,779 A | 7/1996 | Dahl et al. |
| 5,545,183 A | 8/1996 | Altman |
| 5,551,426 A | 9/1996 | Hummel et al. |
| 5,551,427 A | 9/1996 | Altman |
| 5,569,272 A | 10/1996 | Reed et al. |
| 5,584,879 A | 12/1996 | Reimold et al. |
| 5,618,310 A | 4/1997 | Ger et al. |
| 5,649,906 A | 7/1997 | Gory et al. |
| 5,658,327 A | 8/1997 | Altman et al. |
| 5,662,698 A | 9/1997 | Altman et al. |
| 5,674,272 A | 10/1997 | Bush et al. |
| 5,676,850 A | 10/1997 | Reed et al. |
| 5,697,909 A | 12/1997 | Eggers et al. |
| 5,713,863 A | 2/1998 | Vigil et al. |
| 5,725,567 A | 3/1998 | Wolff et al. |
| 5,749,890 A | 5/1998 | Shaknovich |
| 5,769,883 A | 6/1998 | Buscemi et al. |
| 5,824,030 A | 10/1998 | Yang et al. |
| 5,837,007 A | 11/1998 | Altman et al. |
| 5,843,169 A | 12/1998 | Taheri |
| 5,879,349 A | 3/1999 | Edwards |
| 5,891,108 A | 4/1999 | Leone et al. |
| 5,899,917 A | 5/1999 | Edwards et al. |
| 5,910,144 A | 6/1999 | Hayashi |
| 5,938,659 A | 8/1999 | Tu et al. |
| 5,941,845 A | 8/1999 | Tu et al. |
| 5,944,715 A | 8/1999 | Goble et al. |
| 5,954,761 A | 9/1999 | Machek et al. |
| 5,964,756 A * | 10/1999 | McGaffigan et al. .......... 606/41 |
| 6,009,877 A | 1/2000 | Edwards |
| 6,010,531 A | 1/2000 | Donlon et al. |
| 6,012,457 A | 1/2000 | Lesh |
| 6,030,384 A | 2/2000 | Nezhat |
| 6,086,582 A | 7/2000 | Altman et al. |
| 6,086,586 A | 7/2000 | Hooven |
| 6,102,887 A | 8/2000 | Altman |
| 6,106,524 A * | 8/2000 | Eggers et al. ................. 606/50 |
| 6,161,029 A | 12/2000 | Spreigl et al. |
| 6,179,858 B1 | 1/2001 | Squire et al. |
| 6,206,914 B1 | 3/2001 | Soykan et al. |
| 6,210,392 B1 | 4/2001 | Vigil et al. |
| 6,224,491 B1 | 5/2001 | Hiromi et al. |
| 6,224,626 B1 | 5/2001 | Steinke |
| 6,231,570 B1 | 5/2001 | Tu et al. |
| 6,236,891 B1 | 5/2001 | Ingle et al. |
| 6,254,632 B1 | 7/2001 | Wu et al. |
| 6,267,776 B1 | 7/2001 | O'Connell |
| 6,283,992 B1 | 9/2001 | Hankh et al. |
| 6,293,964 B1 | 9/2001 | Yadav |
| 6,296,630 B1 | 10/2001 | Altman et al. |
| 6,305,378 B1 | 10/2001 | Lesh |
| RE37,463 E | 12/2001 | Altman |
| 6,346,099 B1 | 2/2002 | Altman |
| 6,358,247 B1 | 3/2002 | Altman et al. |
| 6,438,427 B1 | 8/2002 | Rexhausen et al. |
| 6,443,949 B2 | 9/2002 | Altman |
| 6,500,186 B2 | 12/2002 | Lafontaine et al. |
| 6,503,247 B2 | 1/2003 | Swartz et al. |
| 6,572,652 B2 | 6/2003 | Shaknovich |
| 6,622,731 B2 * | 9/2003 | Daniel et al. ................ 128/898 |
| 6,702,844 B1 | 3/2004 | Lazarus |
| 6,723,092 B2 | 4/2004 | Brown et al. |
| 6,962,587 B2 * | 11/2005 | Johnson et al. ................ 606/41 |
| 2001/0044619 A1 | 11/2001 | Altman |
| 2002/0010462 A1 | 1/2002 | Altman |
| 2002/0019623 A1 | 2/2002 | Altman et al. |
| 2002/0026228 A1 | 2/2002 | Schauerte |
| 2002/0026233 A1 | 2/2002 | Shaknovich |
| 2002/0077691 A1 | 6/2002 | Nachtigall |
| 2002/0120261 A1 | 8/2002 | Morris et al. |
| 2002/0120263 A1 | 8/2002 | Brown et al. |
| 2002/0151918 A1 | 10/2002 | Lafontaine et al. |
| 2003/0069606 A1 | 4/2003 | Girouard et al. |

FOREIGN PATENT DOCUMENTS

| | | |
|---|---|---|
| EP | 0 558 352 A1 | 9/1993 |
| EP | 0 601 338 A1 | 6/1994 |
| WO | WO94/07564 A2 | 4/1994 |
| WO | WO99/55254 A1 | 11/1999 |
| WO | WO 00/36997 A1 | 6/2000 |
| WO | WO 01/19269 A1 | 3/2001 |
| WO | WO 01/26585 A1 | 4/2001 |
| WO | WO 01/26727 A1 | 4/2001 |
| WO | WO 02/00273 A2 | 1/2002 |
| WO | WO 02/24106 A2 | 3/2002 |
| WO | WO 02/071980 A2 | 9/2002 |
| WO | WO 03/003948 A1 | 1/2003 |

OTHER PUBLICATIONS

*The Thoracic And Cardiovascular Surgeon*, III Supplement, vol. 47, Aug. 1999, pp. 352-356 "Catheter Ablation Of Pulmonary Vein Foci For Atrial Fibrillation".

*The New England Journal Of Medicine*, vol. 339, Sep. 3, 1998, pp. 659-666 "Spontaneous Initiation Of Atrial Fibrillation By Ectopic Beats Originating In The Pulmonary Veins".

*European Journal Of Cardio-Thoracic Surgery*, vol. 11, Apr. 4, 1997 (ISSN 1010-7940), pp. 714-721 "Inhibition Of Atrial Fibrillation By Pulmonary Vein Isolation And Auricular Resection—Experimental Study In A Sheep Model".

*Cleveland Clinic Journal Of Medicine*, vol. 53, No. 1, Jan. 2001 (ISSN 0891-1150), "Radiofrequency Ablation Of The Pulmonary Veins: Can It Stop Atrial Fibrillation At Its Source?"

*Journal Of Computer Assisted Tomography*, vol. 25, No. 1, Jan./Feb. 2001, pp. 34-35 "Identification Of Pulmonary Vein Stenosis After Radiofrequency Ablation For Atrial Fibrillation Using MRI".

*Pacing And Clinical Electrophysiology*, Nov. 2000, vol. 23, No. 11, Part II, pp. 1836-1838 "Pulmonary Veins-Left Atrial Junction: Anatomic And Histological Study".

* cited by examiner

METHODS AND DEVICES FOR CREATING ELECTRICAL BLOCK AT SPECIFIC SITES IN CARDIAC TISSUE WITH TARGETED TISSUE ABLATION

RELATED APPLICATIONS

This application claims priority to U.S. Provisional Application Ser. No. 60/514,428 filed Oct. 24, 2003 entitled Methods And Devices For Creating Electrical Block At Specific Sites In Cardiac Tissue With Targeted Tissue Ablation and is hereby incorporated by reference.

BACKGROUND OF THE INVENTION

In the field of electrophysiology, there are numerous methods that seek to create blocks of specific electrical pathways for the treatment of atrial arrhythmias. These methods primarily rely on applying energy to the tissue to ablate the tissue and thereby block a pathway for electrical conduction. These techniques are used most often in the left or right atriums and can be used to create electrical block either at discrete sites or along linear paths. Examples of such techniques can be seen in prior art U.S. Pat. Nos. 6,237,605; 6,314,962; 6,527,769, 6,502,576 all of which are incorporated herein by reference.

In a usage that is increasing in popularity, the ablation devices used in these methods are introduced percutaneously and advanced into the right atrium via the vena cava and possibly into the left atrium by a trans-septal sheath. These devices are then maneuvered inside the appropriate chamber of the heart by torquing the shaft of the catheter and deflecting the tip to bring the ablation tip in contact with the desired site. Since the atria are relatively large chambers and are moving with the beating of the heart, it is difficult, however, to position these devices accurately.

The most common method of creating an electrical conduction block is by acutely ablating the tissue at the site where the energy delivery catheter is positioned using RF energy, microwave energy, ultrasonic energy or freezing (i.e., cryoablation). These methods typically involve applying a specified energy to the device resting against the endocardial surface of the tissue for a specified time and then reevaluating the region of the ablation to see if the desired electrical conduction block has been created. The result is the formation of an ablation region that extends from the endocardial surface of the cardiac tissue to a tissue depth that is dependant on the amount of energy that is applied.

These methods have proven to be not only very time consuming but also have become characterized with uncertainty as to whether the appropriate amount of ablation has been performed or if the desired target location is being ablated. For example, the resulting depth of the ablation may extend beyond the targeted tissue and injure adjacent tissue such as the esophagus, the trachea or the bronchial tubes. This can happen because of a varying wall thickness of the target cardiac tissue and because other variables (e.g., variation in the electrical impedance of the tissue) can alter the "burn" depth even when time and energy are controlled.

Other possible adverse outcomes of not successfully ablating the desired target site or ablating too much or too little include: not successfully blocking the electrical pathway, disrupting the wrong pathway or creating stenosis in a vessel such as a pulmonary vein.

Of these adverse outcomes, creating a stenosis is a particularly serious complication. As a result, many doctors try to limit their treatment to the wall of the atrium around the ostium of the pulmonary veins to minimize the risk of creating a stenosis in the pulmonary veins. Stenoses as a result of this type of energy ablation in the pulmonary veins has been reported in a small percentage of cases, however it is uncertain if these stenoses are caused more by excessive ablation, missing the appropriate target site or are an inherent risk for this type of treatment in the pulmonary veins.

Turning back to how the known ablation techniques are implemented, current ablation systems typically are maneuvered by twisting or pushing the device shaft or deflecting the distal end to bring this distal end in contact with the desired site for ablation while this distal end is free in the space of the atrium. The motion of the heart makes it very difficult to accurately control the position of the device in this way. Other systems have been proposed that are intending to seat into the pulmonary veins and then create a circumferential ablation around the pulmonary vein which has been engaged. Examples of such systems are disclosed in U.S. Pat. Nos. 6,117,101 and 6,605,085, each of which are incorporated herein by reference.

These concepts address some of the problems with locating the ablation elements relative to the pulmonary vein but are potentially limited in that they presume a round pulmonary vein and are geared towards making a circumferential ablation around the veins. These systems are not optimally suited for creating focal ablations of discrete points or for making linear lesions other than the circumferential lesions around the device location. They also rely upon these same energy delivery mechanisms as the means to create the electrical block.

There are also systems that use a surgical approach to apply the ablation devices to the endocardial surface of the heart. While these approaches can address some of the limitations discussed above, they require a much more invasive access. They also often are characterized by the same drawbacks discussed above, e.g., determining the correct location, determining the correct depth of burn, etc.

For at least these reasons, there is a need for a system that provides means to create the desired electrical block in the cardiac tissue by ablating the necessary tissue while minimizing the risk of ablating too much or too little of the cardiac tissue. There is also a need for a system that minimizes the risk of ablating structures beyond the targeted cardiac wall.

OBJECTS AND SUMMARY OF THE INVENTION

In view of the foregoing, it is an object of the present invention to overcome the limitations of the prior art.

It is a further object of the present invention to provide a more precise ablation device and technique to create electrical block.

It is yet a further object of the present invention to provide a device which creates focused ablation damage to tissue.

It is yet a further object of the present invention to provide a device which allows a user to easily create linear ablation scars.

It is a further object of the present invention to provide a device that more reliably creates electrical block in cardiac tissue.

In one embodiment, the present invention attempts to achieve these objects by providing a bipolar ablation device with multiple needle electrodes that penetrate a desired target tissue. These electrodes may be arranged in a variety of therapeutically effective arrangements, such as a comb-like shape, a multi-needle wheel, or an expanding bow design. By contacting and preferably penetrating the cardiac tissue with bipolar electrodes, a user can more precisely create ablation-induced scarring and thus electrical block at desired target locations without causing unwanted damage and related complications.

DETAILED DESCRIPTION OF THE INVENTION

As previously described, there are a number of mechanisms used to create electrical block acutely. Some of these mechanisms involve the use of energy delivery such as RF or microwave radiation to ablate a target tissue. In these instances, energy is typically applied to either the endocardial or epicardial surface using mono-polar devices.

More specifically, the ablation energy is delivered through a small surface area ablation tip and transmitted through the tissue to a large area ground plate in contact with the body at a far removed site. The result is a concentration of the ablative current immediately around the ablation tip that rapidly decreases as the current travels further into the tissue, away from the ablation tip.

Figure 1A:
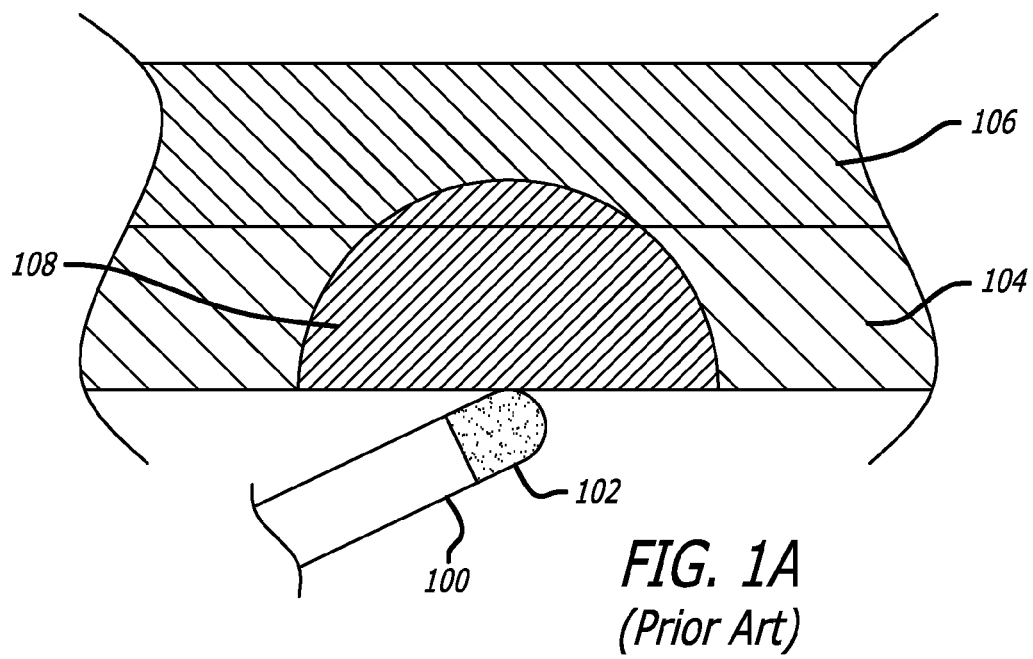
FIG. 1A illustrates a side view of a prior art mono polar electrode.
Figure 1B:
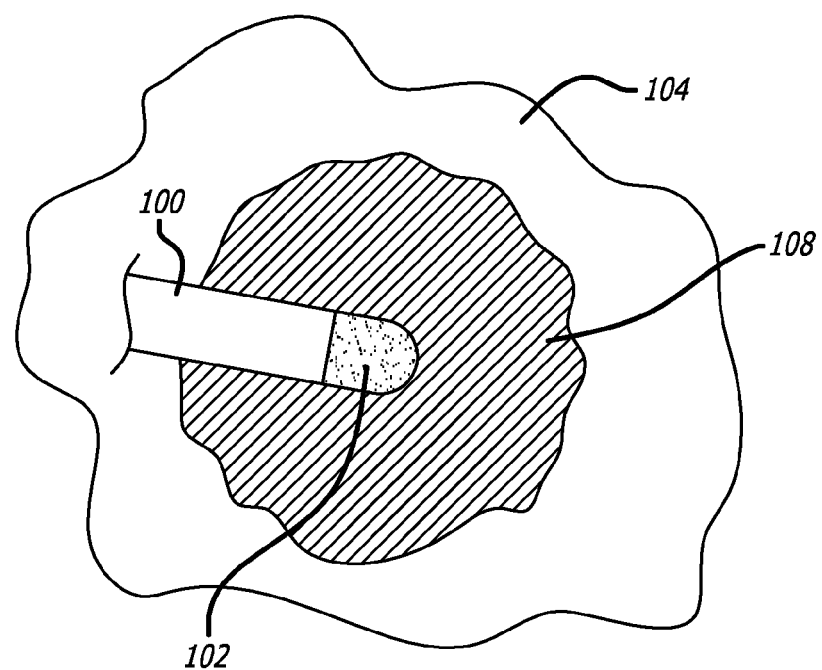
FIG. 1B illustrates a top view of the prior art mono polar electrode of FIG. 1A.

FIGS. 1A and 1B illustrate this concept, depicting a mono-polar ablation device 100 with an ablation tip 102 contacting the tissue wall 104 of tissue 106. In most practices, it is believed that it is necessary for the lines of burns to be fully transmural for effective isolation. With the hemispherical shape of the discrete burns, this requires either overlap of the burns or burn depths beyond the targeted wall thickness. When activated, the ablation tip 102 creates an area of ablated tissue 108, spreading out in a generally radial or spherical pattern. The ablative current immediately near the ablation tip 102 begins relatively strong while spreading out in all directions, yet decreases as the distance from the ablation tip 102 increases. As the strength of the ablative current decreases, so does the amount of ablative damage created by the current.

Also, the ablated tissue is created in a generally circular or spherical pattern within the tissue wall 104 and tissue 106. As a result, a mono-polar ablation device is not capable at creating a region of ablated tissue with great precision. Thus, some non-target tissue areas may be accidentally ablated, while other target tissue areas may not be ablated enough to create a desired electrical block.

Figure 2A:
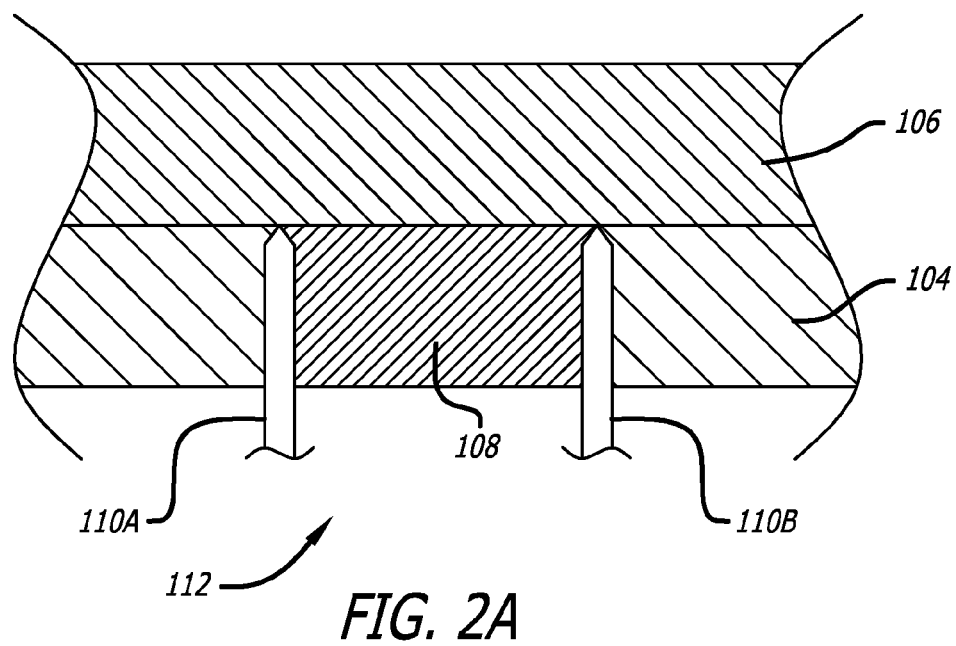
FIG. 2A illustrates a side view of penetrating bipolar electrodes according to the present invention.
Figure 2B:
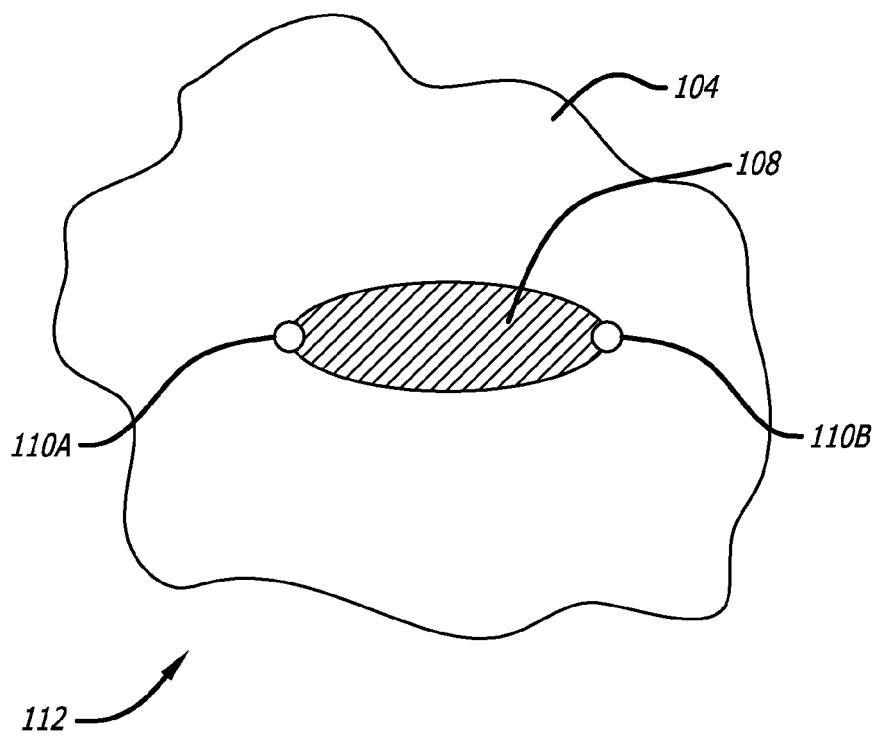
FIG. 2B illustrates a top view of the penetrating bipolar electrodes of FIG. 2A.

To overcome this apparent deficiency in mono-polar ablation techniques, reference is made to FIGS. 2A and 2B which illustrate a bipolar ablation device 112 having a positive piercing electrode 110A and a negative piercing electrode 110B. When activated, ablative current passes from the negative piercing electrode 110B to the positive piercing electrode 110A, following a relatively direct route. Such a short, direct ablative current route provides a more consistent concentration of current within the tissue wall 104 and tissue 106, and therefore a more consistent and narrow area of ablated tissue 108. Additionally, the bipolar ablation device 112 requires less energy to achieve a desired ablated tissue 108 result when compared to a typical mono-polar ablation device 100, since a smaller area is ultimately ablated.

In this respect, bipolar ablation devices 112 allow a user to more precisely create regions of ablated tissue 108, and therefore electrical block. This basic technique can improve the uniformity of the ablation and decrease the amount of tissue ablated to create the same electrical isolation. Such an approach can be used in a surgical approach on either the endocardial or epicardial surface either alone or as an adjunctive procedure to other surgical procedures such as mitral valve repair or coronary bypass surgery. The technique can also be used in a percutaneous approach.

The bipolar ablation technique in accordance with the present invention can also be used in association with other approaches and implants to treat conditions such as atrial arrhythmias. Examples of other approaches in which bipolar ablation in accordance with the present invention may be adjunctive are disclosed in co-pending and commonly owned patent applications including, U.S. patent application Ser. Nos. 10/192,402 entitled Anti-Arrhythmia Devices and Methods of Use filed Jul. 8, 2002; 10/792,111 entitled Electrical Block Positioning Device And Method Of Use Therefor filed Mar. 2, 2004; 10/835,697 entitled Methods And Devices For Creating Electrical Block At Specific Targeted Sites In Cardiac Tissue filed Apr. 30, 2004, each of which is incorporated herein by reference.

Electrode Comb Ablation Devices

The previously described bipolar ablation technique is further refined, according to the present invention, by utilizing different therapeutic electrode and device configurations. For example, one preferred embodiment illustrates a comb ablation device 130, including positive comb 132A and negative comb 132B having needle electrodes 134A and 134B respectively. The needle electrodes 134A and 134B are generally parallel and offset from each other and electrically wired to have a negative polarity, in the case of needle electrodes 134B, and a positive polarity in the case of the needle electrodes 134A. The actual current path between the needle electrodes 134A and 134B could likely form a zig-zag pattern, but for most cases, the spacing between the combs and the barbs would be such that the entire area between the combs would be ablated.

The comb ablation device 130 provides a narrow, concentrated area of current within the target area. The needle electrodes 134A and 134B penetrate the tissue wall 104 and optionally deeper into the tissue 106, creating a deeper area of ablated tissue 108 and therefore more effectively block electrical signals.

In one preferred embodiment, the needle electrodes 134A and 134B are spaced about 3 mm apart, having lengths from about 1 mm to 4 mm.

The needle electrodes 134A and 134B have a generally pointed needle shape, suitable for puncturing tissue 104 and 106. However, other electrode shapes are also preferred, according to the present invention.

Figure 4:
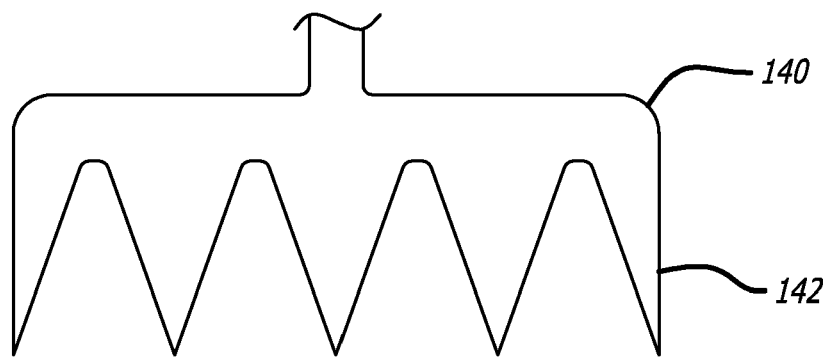
FIG. 4 illustrates a side view of an ablation device according to the present invention.

For example, FIG. 4 illustrates triangular electrodes 142 on comb ablation device 142. The wider triangular shape of the triangular electrodes 142 may allow for a more shallow tissue penetration depth, resulting in shallow ablation and tissue scarring.

Figure 5:
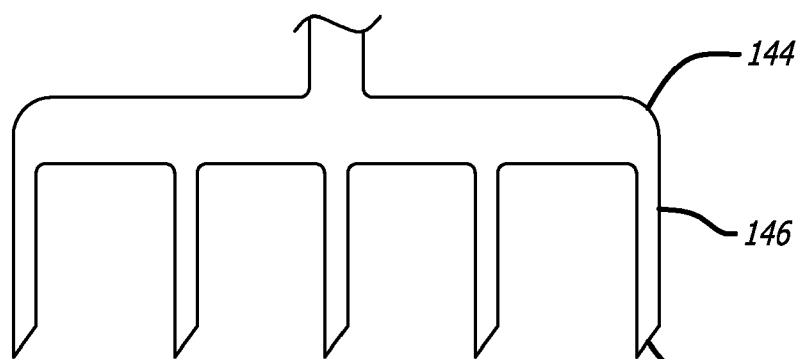
FIG. 5 illustrates a side view of an ablation device according to the present invention.

FIG. 5 illustrates another preferred embodiment of a comb ablation device 144 with narrow electrodes 146. The narrow electrodes 146 have a slender body terminating in an angled tip 146A, allowing for deep penetration and ablation of the tissue wall 104 and tissue 106.

Figure 6:
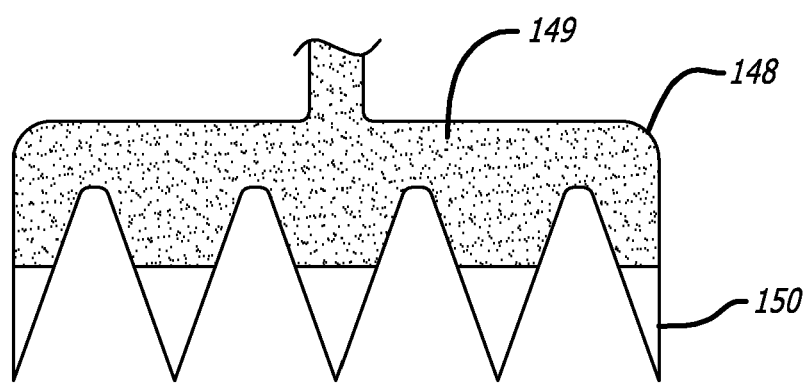
FIG. 6 illustrates a side view of an ablation device according to the present invention.

In addition to varying the shape of the electrode, the conductivity may also be varied to create different ablation characteristics in the target area. For example, FIG. 6 illustrates a comb ablation device 148 with a nonconductive coating 149 disposed over most of the device 148 except a portion of the triangle electrode tips 150. This arrangement allows the triangle electrode tips 150 to penetrate with tissue wall 104 and tissue 106 while primarily directing current to an area below the tissue surface. This can be beneficial in minimizing the severity of the burning on the endocardial surface to minimize the proliferative healing response in the blood flow lumen which could result in stenosis of blood conduits such as the pulmonary veins.

Figure 3A:
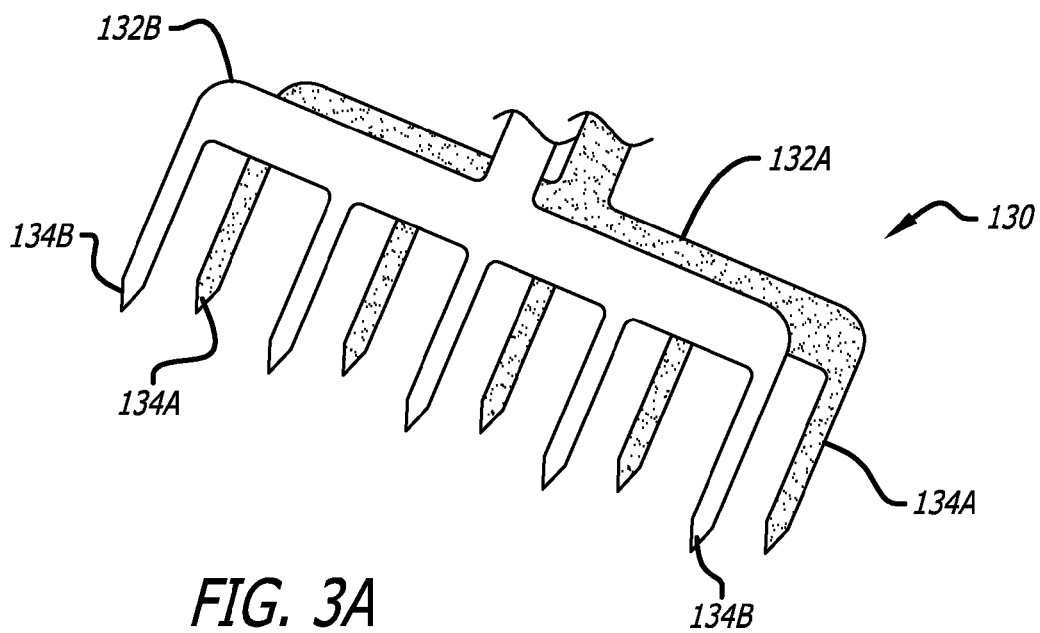
FIG. 3A illustrates a side view of an ablation device according to the present invention.
Figure 3B:
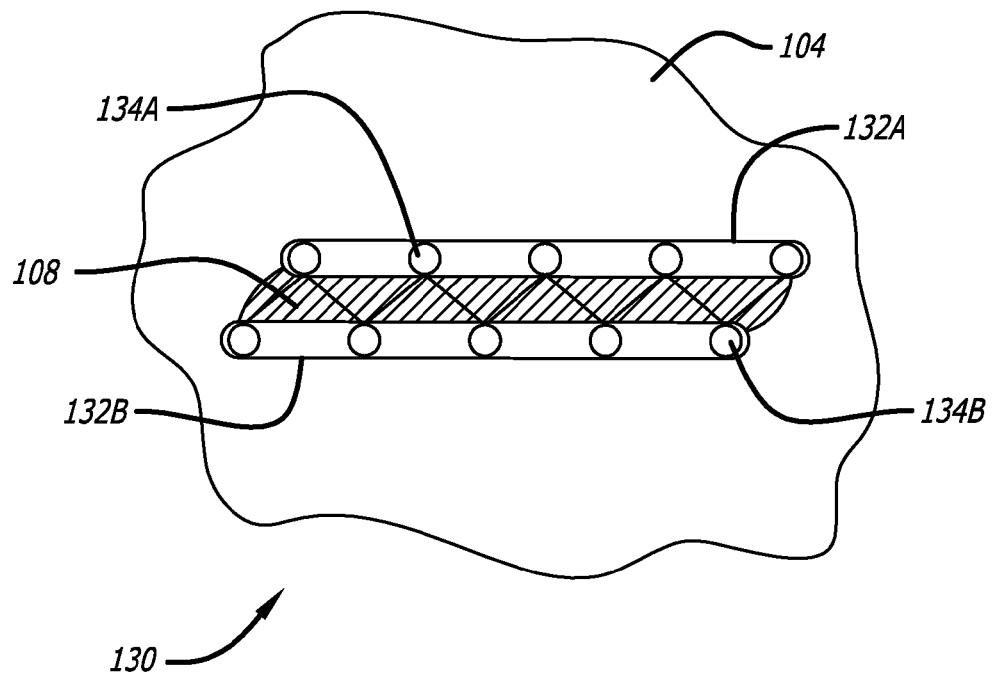
FIG. 3B illustrates a top view of the ablation device of FIG. 3A.

Returning to FIGS. 3A and 3B, the comb ablation device 130 is operated by piercing the tissue wall 104 at a target site of a patient, such as an ostium of a pulmonary vein, and applying current to the device 130 which travels from the positive needle electrodes 134A to the offset negative needle electrodes 134B. The current ablates the tissue wall 104 and possibly the tissue 106, later creating scarring and blocking electrical signals.

Electrode Wheel Ablation Devices

Figure 7A:
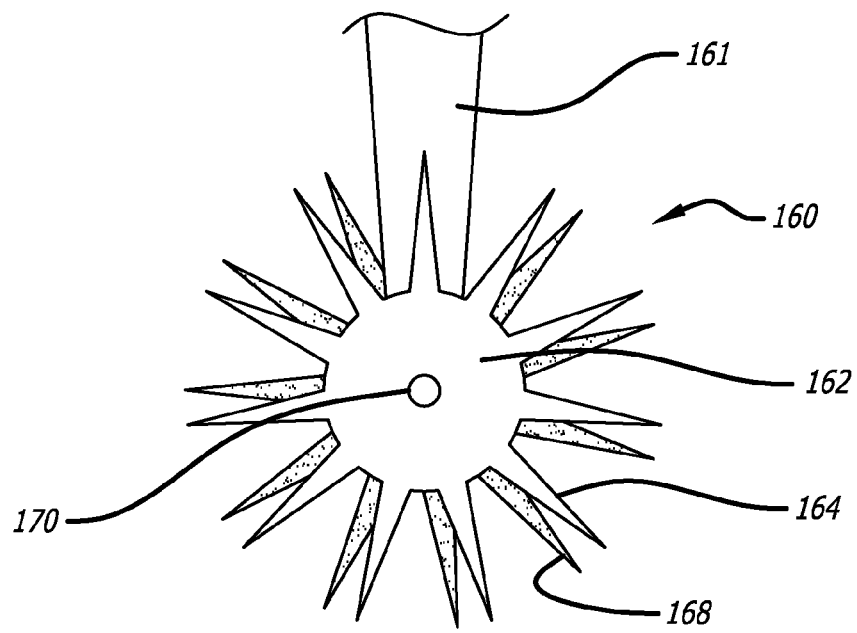
FIG. 7A illustrates a side view of an ablation device according to the present invention.
Figure 7B:
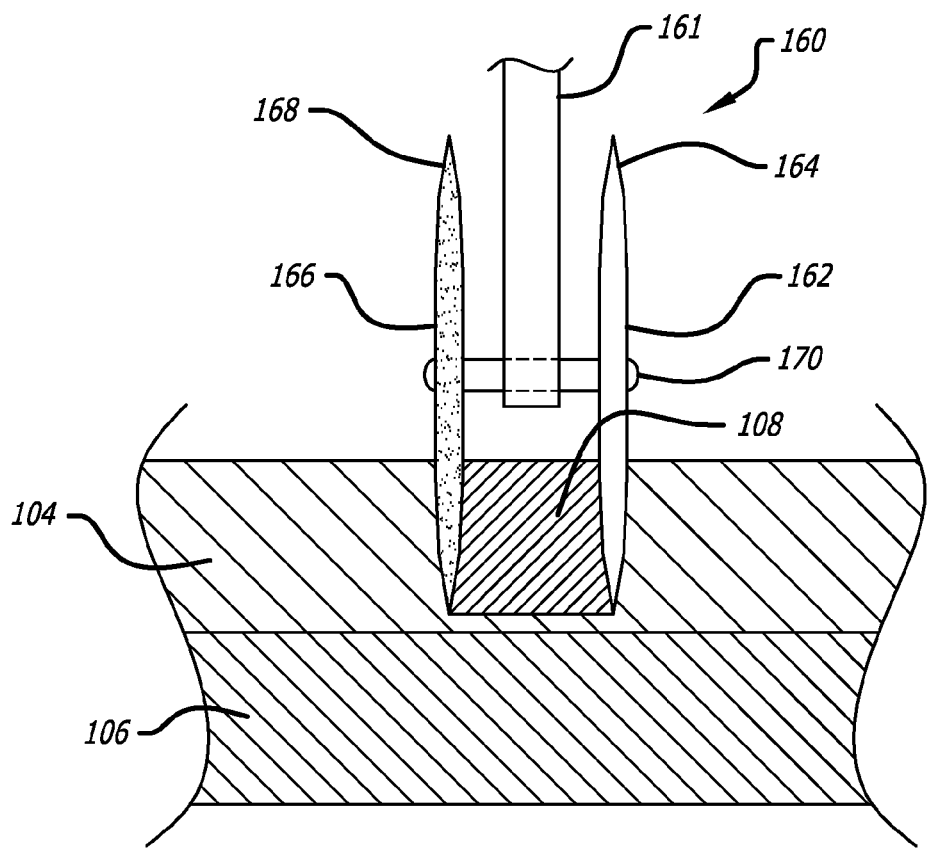
FIG. 7B illustrates a front view of the ablation device of FIG. 7A.

Turning to FIGS. 7A and 7B, a preferred embodiment of an electrode wheel ablation device 160 is illustrated according to the present invention. The electrode wheel ablation device 160 has an overall shape similar to a "pizza cutter", including a body 161 with a positive electrode wheel 162 and a negative electrode wheel 166 rotatably connected by axle 170. The positive electrode wheel 162 includes needle electrodes 164 which are wired to have a positive polarity, while the negative electrode wheel 166 includes needle electrodes 168 which are wired to have a negative polarity.

As with preferred embodiments described elsewhere in this application, the present preferred embodiment penetrates the tissue wall 104 and possibly the tissue 106 with the electrodes 164 and 168, creating an area of ablated tissue 108 between the two wheels 162 and 168 as current passes between each. The rotatable nature of the wheels 162 and 168 allows a user to create a line of ablation by merely rolling the device 160 while in an active electrical state. In this respect, a user may create a precise and relatively narrow area of electrical block, allowing for the creation of straight lines, tight turns, or any other difficult line shape.

In a preferred embodiment, the needle electrodes 134A and 134B are spaced about 3 mm apart, having lengths between about 1 mm and 4 mm.

Figure 8:
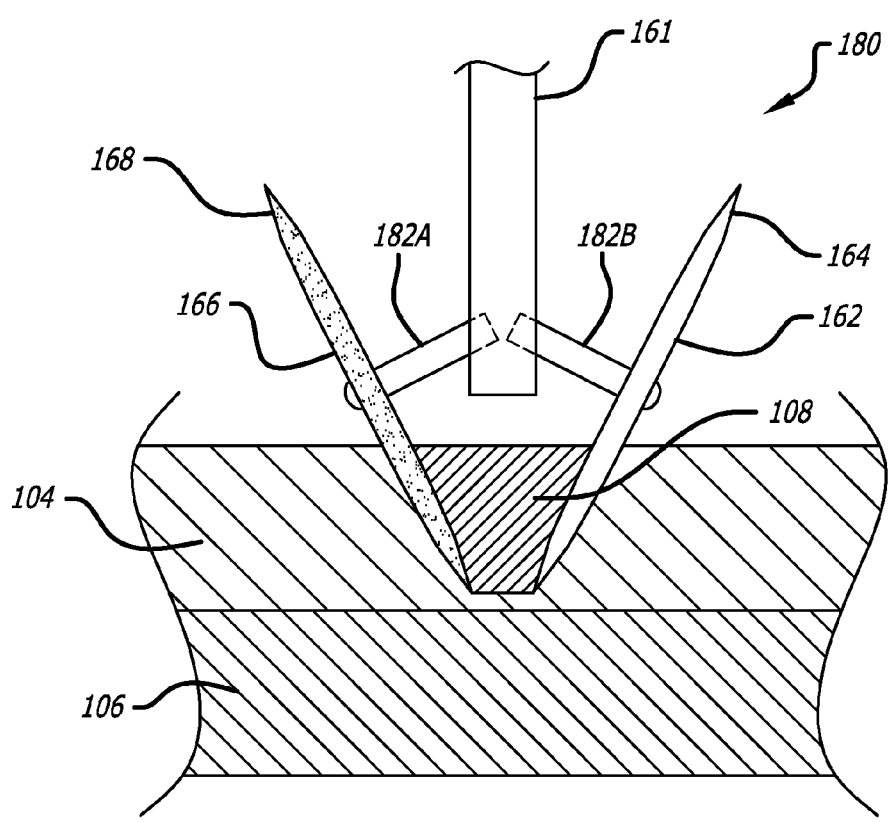
FIG. 8 illustrates a front view of an ablation device according to the present invention.

FIG. 8 illustrates a "pizza cutter" design similar to the previously described embodiment. However, the wheels 162 and 166 of the angled electrode ablation device 180 are rotatably mounted to angled, independently mounted axles 182A and 182B. This arrangement configures the wheels 162 and 166 to form a V-shape.

The electrodes 164 and 168 are angled to move closest to each other near the bottom, increasing in distance towards the upper end. This arrangement results in lower resistance between the tips of electrodes 164 and 168 compared with other areas within the tissue 104, 106. Since the wheels 162, 166 and electrodes 164, 168 have a greater contact area with the tissue wall 104 near the surface, the resistance is decreased, allowing more current and stronger ablation in that area. The V-shaped arrangement may be configured to substantially offset this effect by decreasing the distance between the tips of the electrodes 164, and therefore decrease the resistance.

Note that it may also be desired to have the current flow disproportionately higher on either the epicardial or endocardial side of the tissue wall 104. These variables allow the current to be focused where desired through the thickness of the tissue wall 104.

Bow Electrode Ablation Device

Figure 9:
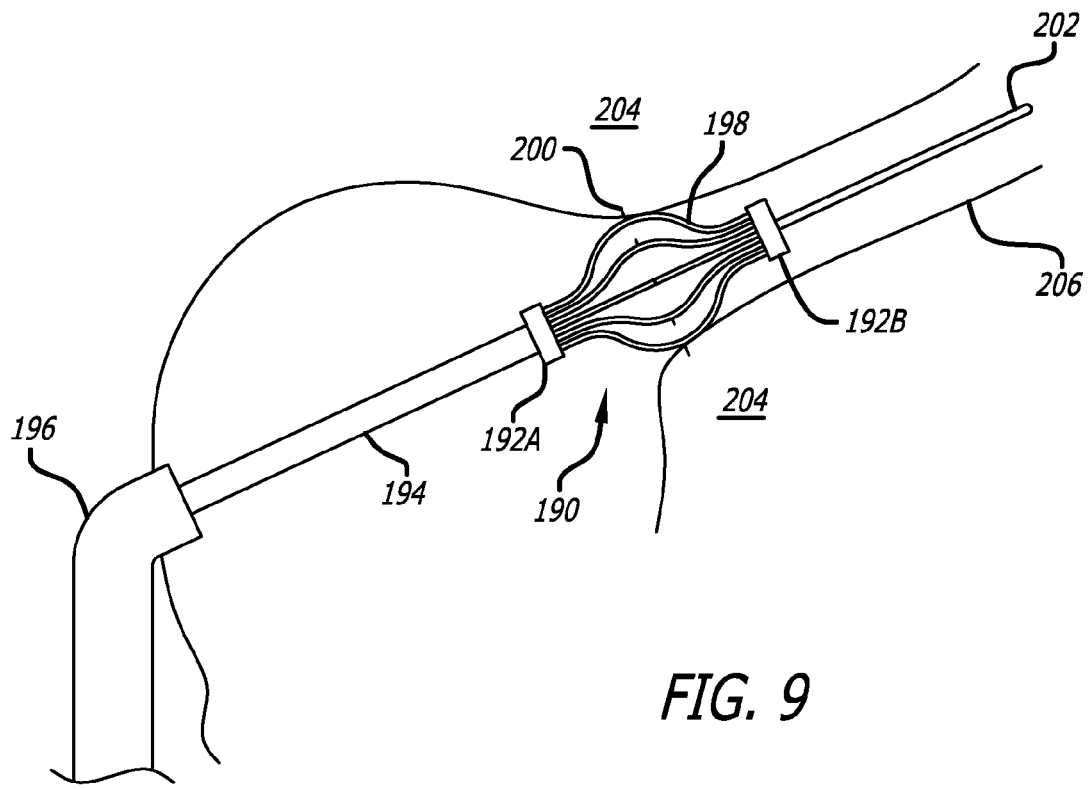
FIG. 9 illustrates a side view of a percutaneous ablation device according to the present invention.

In another preferred embodiment according to the present invention, FIG. 9 illustrates a bow electrode ablation device 190, configured for a percutaneous treatment approach. In this example, a catheter body 194 includes an expandable region of bow electrodes 198 which expand to ablate the ostium 204 or possibly the inside surface of the pulmonary vein 206.

Each bow electrode 198 is fixed to a proximal hub 192A and distal hub 192B, having a barb 200 directed perpendicularly to pierce and therefore engage the ostium 204. The bow electrodes 198 expand to a ball or bulb shape by the movement of one of the hubs 192A or 192B. For example, the proximal hub 192A may slide in a distal direction, pushing the bow electrodes 198 outward, or the distal hub 192B may slide in a proximal direction, pushing the bow electrodes 198 outward. In either case, an inner control wire allows a user to control this expansion or retraction. Thus, the bow electrodes 198 can be advanced in their collapsed state into the ostium 204 of the pulmonary vein 206. Alternatively, the bow electrodes 198 can be formed such that their relaxed state is in the expanded position and they can be constrained to a smaller diameter for introduction and removal by means of a retractable sleeve.

The bow electrodes 198 are wired at their proximal ends such that alternating bows 198 have alternating polarity. The bulk of the length of the bow is preferably coated with electrical insulation allowing only the bare metal of barb 200 to be exposed. The bow electrode ablation device 190 is delivered to the ostium 204 of a pulmonary vein 206 by an aortic sheath 196 positioned through an aortic wall. The distal guide portion 202 directs the catheter body 194 into the pulmonary vein 206, allowing the bow electrodes 198 to be positioned and expanded at a desired target area.

Once in a desired position, energy can then be applied, with every other electrode 198 acting as a positive pole, while the others act as a negative pole. The current then passes from the electrodes 198 with positive polarity to the electrodes 198 with negative polarity, on either side. As with the previously described examples, the current ablates the tissue of target area, in this case creating a circumferential burn along the ostium 204.

It is anticipated that other geometries of the barbs 200 could be used to facilitate piercing of the ostium 204 of the pulmonary vein 206. For example, the electrode shapes seen in FIGS. 4–6 may be adapted for use as the barbs 200.

It is also anticipated that this same technique could be used with a smaller number of barbs 200 to create a burn line along a segment of tissue without completely surrounding the pulmonary vein 206. Further, it is also anticipated that an ablation line could be created in a line along the atrial wall not adjacent to the pulmonary veins 206, by a collapsible configuration of the embodiment illustrated in FIGS. 3A–6.

This basic concept of using bipolar energy ablation with piercing electrodes could potentially be used with any of the wavelengths of energy described earlier since the basic advantage is driven by the electrode geometry and location in the tissue and is essentially independent of the energy wavelength. Though the examples described and shown are often illustrated for only one type of electrode, it is understood that these are only examples and the same techniques can be applied for the other types of electrodes.

The concept of using bipolar energy ablation has numerous potential applications. In addition to treating atrial arrhythmias as discussed above, another preferred embodiment is in the performance of deep tissue ablation in, for example, the treatment of ventricular arrhythmias where the ventricular wall can be relatively thick. The discrete and precise nature of ablation that is enabled by bipolar ablation in accordance with the present invention provides advantages over mono-polar ablation where the degree of ablation will vary according to proximity of the tissue to the mono-polar ablation electrode.

Ablation Tissue Targeting

Figure 10:
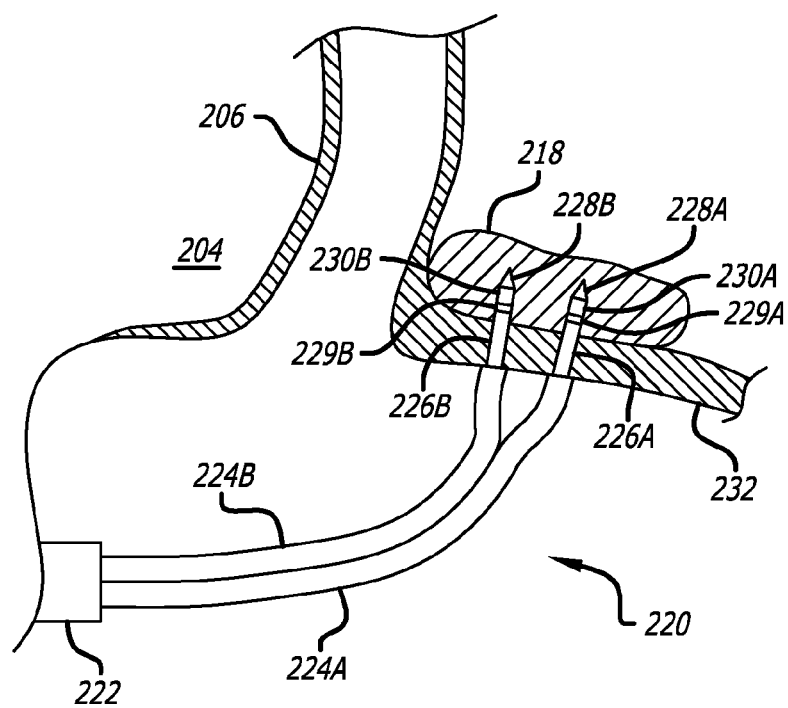
FIG. 10 illustrates a side view of a percutaneous ablation device according to the present invention.

In yet another preferred embodiment of the present invention, FIG. 10 illustrates a tissue targeting ablation device 220 that allows a user to "target" specific types of tissue and therefore more precisely ablate an intended target area. Specifically, the tissue targeting ablation device 220 is composed of a main sheath 222 that contains two catheters 224a and 224b. Each catheter 224a and 224b includes an electrode needle 226a and 226b, respectively, having a sharpened electrode tip 228a, 228b and a ring electrode 229a, 229b, separated by a nonconductive polymer ring 230a, 230b. [In one embodiment, one electrode tip 228a has a positive polarity and the other electrode tip 228b has a negative polarity so that bi-polar ablation can be performed between the two needle tips. However, mono-polar ablation is also contemplated with this design.

In one embodiment, the needle electrodes 226a, 226b are preferably 0.020" (25 gage) in diameter, while the polymer rings 230a, 230b are about 0.020" in length. The electrode tip 228a, 228b and the ring electrode 229a, 229b on each needle 226a and 226b are independent, electrically isolated electrodes that are coupled to wires that exit at a proximal end of the catheter 224a, 224b and ultimately connect to a device which produces ablative current and also measures impedance.

Generally speaking, the impedance of the surrounding tissue is measured between the electrodes on each catheter 224a and 224b. For example, the impedance could be measured between the electrode tip 228a and ring electrode 229a. Since fat, muscle, and blood all have different impedance values, these measurements can be used to determine if the electrode needles 226a and 226b are positioned within a desired target tissue.

This tissue-targeted ablation is particularly useful when ablating a specific body structure while minimizing the damage to adjacent structures. In one specific example, the tissue-targeted ablation could be used to ablate pulmonary vein ganglia which have been found to be located within fat pads 218 on the epicardial surface at the ostia 204 of the pulmonary vein 206. It is believed that the pulmonary vein ganglia may play a significant role in triggering or sustaining atrial fibrillation and therefore that ablating the ganglia may reduce or eliminate the atrial fibrillation.

In this regard, fat has a much higher impedance and resistance compared with muscular tissue or blood and thus electrical energy applied to tissue generally often avoids the fat tissue. As a result, in an ablation method where the ablation energy is applied either only partially in the fat pad 218 or is applied outside the fat pad, the tissue in the fat pad 218 is mostly avoided by the current. The current thus causes more damage to the muscle tissue 232 than to the fat pad 218.

The electrode needles 226a and 226b as used in connection with this embodiment of the invention can be placed into a specific tissue location, e.g., into a fat pad 218, by measuring the impedance between electrodes 228a, 228b and 229a, 229b, thereby indicating when the electrodes are positioned in fat tissue. In this manner, positioning the electrodes into contact with muscle tissue can be avoided. As a result, when electrical energy is applied, the pulmonary vein ganglia in the fat pad 218 is ablated and significant ablation damage to muscle tissue 232 (as well as other non-target tissues) is substantially avoided.

In operation in another embodiment, the targeting ablation device 220 is introduced trans-septally into a left atrium of a heart by the main sheath 222. The catheters 224a and 224b are advanced from the main sheath 222 and steered to press against the muscle tissue 232 of the heart. Preferably, the steering of catheters 224a and 224b is accomplished by a conventional steerable catheter construction, commonly known in the art, which allows the tip to be flexed.

Next, the electrode needles 226a, 226b are advanced from the catheters 224a and 224b, causing the sharp electrode tips 228a, 228b to penetrate the muscle tissue 232 of the ostia 204. As the electrode needles 226a, 226b are introduced, their impedance readings are monitored. A lower impedance reading may indicate that the electrode needles 226a, 226b are positioned in blood or muscle tissue 232 and a higher impedance reading may indicate a position within fat tissue, such as fat pad 218. A more detailed example technique for finding the desired target site is described by Plaft et al. in their abstract from the 2003 NASPE meeting published in Pacing and Clinical Electrophysiology Apr. 2003, vol. 26, the contents of which are incorporated by reference.

Once the needle electrodes 228a, 228b have been determined to be in a desired target location, such as within fat pad 218, a user may cause ablation to the region. Preferably, bipolar ablation techniques may be used to form an oval shaped burn between some or all of the electrodes 228a, 228b, 229a, 229b on each needle electrode 226a and 226b. However, mono-polar ablation may also be used to achieve a cylinder-shaped therapeutic ablation treatment. Once the desired ablation has been performed, the user may remove the needle electrodes 226a, 226b, the catheters 224a, 224b, and finally the main sheath.

In this respect, the user can create a highly localized ablation burns with the targeting ablation device 220 while minimizing burn damage to the surrounding non-target tissue. This targeted burn is facilitated even for an epicardial target area without requiring more invasive surgical approaches, ultimately leading to a more precise and less invasive approach.

Another specific anatomical application for this type of tissue targeted ablation can be to create an ablation of the muscular tissue of the atrial wall while avoiding the esophagus wall which abuts the atrial wall in some locations.

Note that this impedance targeting approach may be used in conjunction with any of the previously described embodiments of this application, and is especially preferable with percutaneous ablation approaches.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of ablating tissue to treat atrial fibrillation comprising:
    providing at least one tissue penetrating element having an ablation electrode and a ring electrode, said at least one tissue penetrating element being sufficiently small for intraluminal delivery to tissue associated with a pulmonary vein of a cardiovascular system;
    introducing said tissue penetrating element into tissue associated with said pulmonary vein;
    measuring impedance between said ablation electrode and said ring electrode;
    determining the nature of said tissue associated with said pulmonary vein according to said impedance measurement;
    continuing to introduce said tissue penetrating element into said tissue until said impedance measurement indicates that said ablation electrode is located in fat pad tissue associated with said pulmonary vein ablating said fat pad tissue for a sufficient period so as to substantially eliminate said atrial fibrillation.

2. The method according to claim 1, wherein the providing of at least one tissue penetrating element includes providing at least two tissue penetrating elements.

3. The method according to claim 2, wherein ablating said fat pad tissue includes applying bi-polar ablation energy to said tissue region.

4. A method of ablating tissue to treat atrial fibrillation comprising:
    providing at least two tissue penetrating elements, each penetrating element having at least one electrode, said at least two tissue penetrating elements being sufficiently small for intraluminal delivery to tissue associated with a pulmonary vein of a cardiovascular system;
    introducing said at least two tissue penetrating elements into tissue associated with said pulmonary vein;
    measuring impedance between said at least one electrode of each of said at least two tissue penetrating elements;
    determining the nature of said tissue associated with said pulmonary vein according to said impedance measurement;
    continuing to introduce said at least two tissue penetrating elements into said tissue until said impedance measurement indicates that said ablation electrode is located in fat pad tissue associated with said pulmonary vein;
    ablating said fat pad tissue for a sufficient period so as to substantially eliminate said atrial fibrillation.

5. The method according to claim 4, wherein the providing of at least two tissue penetrating elements includes providing two tissue penetrating elements.

6. The method according to claim 5, wherein ablating said fat pad tissue includes applying bi-polar ablation energy to said tissue region.

* * * * *